United States Patent [19]

Sugimoto et al.

[11] 4,057,544

[45] Nov. 8, 1977

[54] α-ALKYLSULFOBENZYL PENICILLINS

[75] Inventors: Keiichi Sugimoto, Kawanishi; Koji Nishijima, Osaka; Hiroshi Akimoto, Nishinomiya; Tadashi Hanaoka, Osaka; Nobuharu Kakeya, Kawanishi, all of Japan

[73] Assignee: Takeda Chemical Industries, Ltd., Osaka, Japan

[21] Appl. No.: 417,527

[22] Filed: Nov. 20, 1973

[30] Foreign Application Priority Data

July 9, 1973 Japan .................................. 48-77262
July 13, 1973 Japan .................................. 48-79606

[51] Int. Cl.² ........................................... C07D 499/46
[52] U.S. Cl. .................................. 260/239.1; 424/271
[58] Field of Search ...................................... 260/239.1

[56] References Cited

U.S. PATENT DOCUMENTS 3,660,379   5/1972   Morimoto et al. ................ 260/239.1
3,697,507   10/1972  Frederiksen et al. ............. 260/239.1
3,748,323   7/1973   Hamanaka ........................ 260/239.1
3,925,362   12/1975  Sugimoto et al. ................ 260/239.1

Primary Examiner—Paul M. Coughlan, Jr.
Attorney, Agent, or Firm—Wenderoth, Lind & Ponack

[57] ABSTRACT

Novel penicillins of the formula

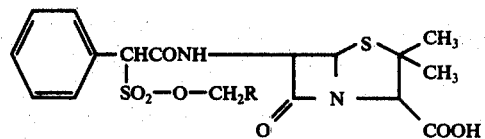

wherein R is a branched chain alkyl group of from 3 to 14 carbon atoms, and their pharmaceutically acceptable salts, are easily absorbed in the blood and tissues through oral administration and show excellent antimicrobial activity against Gram-positive and Gram-negative bacteria, particularly against microorganisms of the genus Pseudomonas, such as *Pseudomonas aeruginosa*.

7 Claims, No Drawings

α-ALKYLSULFOBENZYL PENICILLINS

The present invention relates to new synthetic penicillins useful as antibacterial agents, nutritional supplements in animal feeds, and therapeutic agents in animals, including human beings and poultry. More particularly, the present invention relates to novel penicillin compounds of the general formula I:

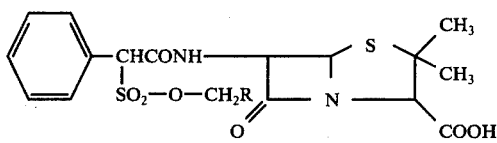

wherein R is a branched chain alkyl group of from 3 to 14 carbon atoms, preferably 4–14 carbon atoms, and their pharmaceutically acceptable salts.

Hitherto, many types of penicillin have been synthesized by N-acylating 6-aminopenicillanic acid or its salt with various carboxylic acids or reactive derivatives thereof. However, most of these known penicillin compounds possess one or more of the following drawbacks: (1) not being effective against Gram-negative bacteria, (2) being ineffective against so-called penicillin G-resistant strains of bacteria, e.g. many strains of *Staphylococcus aureus*, and (3) showing substantially no antimicrobial activity against microorganisms belonging to the genus Pseudomonas.

Among those known penicillins, α-sulfobenzylpenicillin is unique in that the penicillin is free from the abovementioned shortcomings. Thus α-sulfobenzylpenicillin shows quite strong antimicrobial activity against Gram-positive bacteria, Gram-negative bacteria including the genus Pseudomonas, and penicillin G-resistant strains of bacteria. It has however recently been found that this penicillin does not provide a sufficiently high blood concentration when orally administered to hosts, including man.

The present inventors have succeeded in synthesizing novel penicillin compounds of the general formula I as well as their pharmaceutically acceptable salts, and have unexpectedly found that, when orally administered to a host, these novel penicillins are far more easily absorbed in the blood and tissues from the gastrointestinal tract than is the case with α-sulfobenzylpenicillin. That is, the absorption ratio of these penicillins is far higher than that of α-sulfobenzylpenicillin. The present inventors have also found that the penicillins absorbed in the blood and tissues are immediately converted to α-sulfobenzylpenicillin, that this conversion gives a high blood concentration of α-sulfobenzylpenicillin, and that such penicillins are stable, particularly against heat, and afford excellent storage stability when storing in atmospheric surroundings.

They have also found that the penicillin compounds I as well as their pharmaceutically acceptable salts have a very low toxicity to animals, including mammals.

Thereofore, it is the main object of the present invention to provide novel penicillins which are highly efficiently absorbed through oral administration.

Another object of the present invention is to provide novel penicillins showing excellent antimicrobial activity against Gram-positive and Gram-negative bacteria.

Another object of the present invention is to provide novel penicillins having strong antibacterial activity against microorganisms of the genus Pseudomonas, and which are effective against Pseudomonas infections.

Another object of the present invention is to provide an industrially feasible method for the production of these useful penicillins.

A further object of the present invention is to provide a pharmaceutical composition for antibacterial treatment which comprises, as an active ingredient, the penicillin compound I or a pharmaceutically acceptable salt thereof, and a pharmaceutically acceptable carrier therefor, which composition is particularly effective against Pseudomonas infections.

Further objects of the invention, as well as advantages and features thereof, will be apparent from the following description of the invention.

Examples of the branched alkyl group of 3 to 14 carbon atoms as represented by the symbol R include isopropyl, 1,1-dimethylethyl, 1-methylpropyl, 2-methylpropyl, 1,1-dimethylpropyl, 1-methylbutyl, 1,2-dimethylpropyl, 1-ethylpropyl, 2,2-dimethylpropyl, 2-methylbutyl, 3-methylbutyl, 1,1-dimethylbutyl, 1-methylpentyl, 1,3-dimethylbutyl, 1,1,2-trimethylpropyl, 1-ethyl-2-methylpropyl, 4-methylpentyl, 1-ethyl-1-methylpropyl, 1-ethylbutyl, 2-ethylbutyl, 1,1,3-trimethylbutyl, 1-ethyl-3-methylbutyl, 1-ethylpentyl, 2-ethylpentyl, 1,1-dimethylpentyl, 1-(1-methylethyl)-butyl, 1,4-dimethylpentyl, 1,1-diethylpropyl, 5-methylhexyl, 1-(1-methylethyl)-3-methylbutyl, 1,1-dimethylhexyl, 2,4,4-trimethylpentyl, 1,1,4-trimethylpentyl, 1-methylheptyl, 1,5-dimethylhexyl, 1-ethyl-4-methylpentyl, 1,1-diethylbutyl, 1,1-diethyl-2-methylpropyl, 6-methylheptyl, 2-butylpentyl, 1,1,5-trimethylhexyl, 7-methyloctyl, 2-ethyl-5-methylhexyl, 1,1-diethyl-3-methylbutyl, 1-methylnonyl, 8-methylnonyl, 1,1-diethyl-4-methylpentyl, 1-ethyl-5-methyloctyl, 1-methylundecyl, 1-methyl-9-methyldecyl, 2-ethylundecyl, 1-(1-methylethyl)-8-methylnonyl and 1-(1-methylethyl)-undecyl.

The pharmaceutically acceptable salts of the desired compounds include salts with bases such as nontoxic metals, particularly alkali metals and alkaline earth metals (e.g. sodium, potassium, calcium, aluminum, magnesium, etc.), and amines, particularly organic amines (e.g. ammonia, triethylamine, diethanolamine, dibenzylamine or other amines which have been used for various known penicillins).

The penicillin compounds of the general formula I or their pharmaceutically acceptable salts are produced by a method which comprises reacting 6-aminopenicillanic acid, its salt or its easily cleavable ester with a carboxylic acid shown by the general formula II:

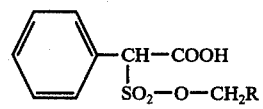

wherein R has the same meaning as defined above, or a reactive derivative thereof, and, when said easily cleavable ester is employed, further removing the easily cleavable group so introduced from the condensation product.

Compounds of general formula II, are novel compounds, and may be prepared by, for example, reacting the silver salt of α-sulfophenylacetic acid with a compound of general formula III:

$$I - CH_2 - R \qquad III$$

wherein R is as previously defined, or alternatively by reacting α-chlorosulfonylphenylacetic acid tertiary butyl ester, which is obtained by reacting α-sulfophenylacetic acid dichloride with tertiary butanol in a non-aqueous solvent such as dichloromethane in the presence of a base such as picoline or triethylamine, with a compound of a general formula IV:

     IV wherein R is as previously defined, in a non-aqueous solvent such as carbon tetrachloride in the presence of a base such as picoline or triethylamine to produce a compound of general formula V:

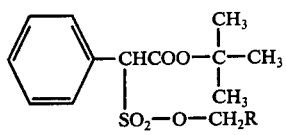     V wherein R is as previously defined, and then subjecting the same to acid hydrolysis in a non-aqueous solvent such as chloroform with concentrated sulfuric acid.

It has been known that various penicillin compounds can be produced by N-acylating 6-aminopenicillanic acid, a salt or easily cleavable ester thereof with a carboxylic acid or a reactive derivative thereof and, when an easily cleavable ester is employed, by further removing the easily cleavable group. Various means and methods for such reactions have so far been well established. The present invention may be carried out in accordance with known N-acylation reaction and techniques therefor.

The salts of 6-aminopenicillanic acid include metal salts (e.g. sodium salt, calcium salt or aluminum salt) or organic amine salts (e.g. triethylamine salt). The easily cleavable ester of 6-aminopenicillanic acid is exemplified by a silyl ester (e.g. trimethylsilyl ester or trimethoxysilyl ester) of 6-aminopenicillanic acid, the polymeric silene ester of 6-aminopenicillanic acid, an alkyltin ester (e.g. tri-n-butyltin ester) of 6-aminopenicillanic acid, an alkylsulfonylalkyl ester (e.g. β-methylsulfonylethyl ester or β-ethylsulfonylethyl ester), an acyloxyalkyl ester (e.g. pivaroyloxymethyl ester, acetoxymethyl ester, propionyloxyethyl ester, butyloyloxymethyl ester or benzoyloxymethyl ester) and a substituted or unsubstituted phenylalkyl ester (e.g. triphenylmethyl ester).

The silyl ester may be mono- or di-ester. The silyl derivative of 6-amino-penicillanic acid is prepared by reacting 6-aminopenicillanic acid with a monofunctional silicone derivative such as trimethylmonochloro silane, trimethoxymonochloro silane or the like in an inert solvent such as chloroform, toluene, benzene, ethyl acetate, or the like, preferably in the presence of a base such as triethylamine or the like.

The polymeric silene ester of 6-aminopenicillanic acid is prepared by reacting 6-aminopenicillanic acid with a difunctional silicone derivative such as dimethyldichlorosilane, dimethoxydichlorosilane or the like in the presence of the base and in the inert solvent. The tin ester of 6-aminopenicillanic acid is produced by reacting 6-aminopenicillanic acid with, for example, tri-n-butyltinoxide. Other easily cleavable esters of 6-aminopenicillanic acid may be produced by known methods.

In the method of the present invention any of those known easily cleavable esters are conveniently employed.

The starting compound II may be in the form of the corresponding salt.

The salt or reactive derivative of the compound shown by the general formula II can be prepared from the compound II by per se known means which have been well established in the field of the penicillin or peptide synthesis. Thus preferable salts of the compound II are exemplified by an inorganic salt (e.g. sodium salt, potassium salt or calcium salt) or an amine salt (e.g. triethylamine salt or pyridine salt), and the reactive derivative of the compound II is exemplified by the corresponding carboxylic acid halide (e.g. chloride), anhydride, mixed anhydride (for example with ethylchlorocarbonate), activated ester or the like. When the compound II in the free or salt form is used for the N-acylation reaction, it is preferable to use a suitable condensing agent, examples of which include an N,N'-di-substituted carbodiimide such as N,N'-dicyclohexylcarbodiimide; azolide such as N,N'-carbonylimidazole, N,N'-thionyldiimidazole, etc.; and a dehydrating agent such as N-ethoxycarbonyl-2-ethoxy-1,2-dihydroquinoline, phosphorus oxychloride, alkoxy acetylene, etc. In these instances of using condensing agents, it is likely that the reaction proceeds via the formation of a reactive carboxylic acid derivative.

Ordinarily, this reaction is more advantageously and smoothly conducted in a solvent, provided it is not detrimental to the reaction. Suitable solvents are exemplified by water and organic solvents such as acetone, tetrahydrofuran, dioxane, acetonitrile, chloroform, dichloromethane, dichloroethane, pyridine, dimethylaniline, dimethylformamide, dimethylacetamide, dimethylsulfoxide, ethyl acetate, benzene, tetrahydrofuran as well as their mixtures.

When the N-acylation reaction is carried out by the reaction between the carboxylic acid II and 6-aminopenicillanic acid in the presence of a condensing agent, an organic solvent such as dimethyl formamide, chloroform, acetone, methylene chloride, methyl isobutyl ketone, dioxane, ethyl acetate or the like is preferred.

When an acid halide of the carboxylic acid II is employed as the reactive derivative of the carboxylic acid II, the N-acylation reaction is preferably carried out in the presence of an organic base such as a tertiary amine (e.g. triethylamine, pyridine, quinoline, isoquinoline or the like) or an inorganic base such as an alkali (e.g. an alkali metal carbonate, an alkali metal hydroxide, an alkali metal bicarbonate, etc.). When the easily cleavable ester of 6-aminopenicillanic acid is employed, the N-acylation reaction is carried out in an inert solvent such as chloroform, methylene chloride, benzene, toluene or the like.

The reaction is ordinarily conducted at a temperature of about −10° C to about 50° C, preferably about −10° C to about 10° C. Usually the reaction goes to completion in about 30 to 90 minutes. It is particularly desirable to conduct the reaction in a non-aqueous, inert organic solvent such as those above mentioned at a temperature ranging from about −10° C to about 10° C.

When the easily cleavable ester of 6-aminopenicillanic acid has been employed for the reaction, the condensation reaction product may be easily freed of the easily cleavable group so introduced, by subjecting the product to procedures which are conventional per se. For instance, when the easily cleavable ester used is a silyl or silene ester, the easily cleavable group introduced can be easily removed by contacting the reaction product or mixture with an alcohol, e.g. methanol or ethanol, or water.

The compounds of the present invention can then be recovered from the reaction mixture in a state of high purity in accordance with per se known means (e.g. extraction, concentration, lyophilization or the like). Usually the desired compound of the present invention can be recovered from the reaction mixture in which they exist either as the free acids or salts thereof. If desired, the salts may be converted into free penicillin or other pharmaceutically acceptable salts by conventional processes, and free penicillin may be converted to the pharmaceutically acceptable salts in accordance with per se known means.

Further, depending upon the requirements, these compounds can be further purified by such procedures as column chromatography, countercurrent distribution, recrystallization and the like.

In the desired penicillins of the present invention, the α-carbon atom of the acyl group constitutes an asymmetric carbon atom and there exists two optical isomers. It is to be understood that all such isomeric forms as well as mixtures thereof are included in the scope of the present invention. When the acylation product is obtained as a mixture of isomers, if desired the mixture may be resolved optically into the respective isomers, for example by chromatography, according to per se known procedures. Alternatively, the optically active penicillins are produced by employing an optically active carboxylic acid of the general formula II or its reactive derivative derived from the carboxylic acid II for the acylation of 6-aminopenicillanic acid, its salt or easily cleavable ester thereof.

The penicillin compounds obtained by the process of this invention can be administered, either as such or after compounding it with pharmaceutical excipients or carriers, in such dosage forms as powders, granules, tablets, capsules, suppositories, injections and so on. The recommended unit dosage amount for an adult human is 0.1 to 1 gram in terms of amount of α-sulfobenzylpenicillin. The unit dosage is administered every 1 to several hours, for example 1-4 hours.

The pharmaceutical compositions such as powders, granules, tablets, capsules, suppositories, etc. can be prepared in accordance with per se known means, for example, by admixing the penicillin of the present invention with the known pharmaceutical excipients or carriers, for example starch.

The objective compounds of this invention are superior in stability in storage as compared to compounds corresponding to general formula I in which R stands for a straight-chain alkyl group, and it is noteworthy that, among the compounds according to this invention, the salts are particularly stable against heat and quite low in their rate of decomposition at room temperature to elevated temperatures near 40° C.

Pharmacological Test

The penicillin compounds prepared by the method of this invention were orally administered to rats (body weights: 200 ± 10 g.) in a dose of 200 mg./kg. as α-sulfobenzylpenicillin disodium salt. The urine excreted during the 15 hours following the administration was collected and the percent urinary recovery of α-sulfobenzylpenicillin disodium salt was determined. The results are set forth below. The quantitative determination of α-sulfobenzylpenicillin disodium salt was performed using *Pseudomonas aeruginosa* NCTC 10490.

As a control, the same amount of α-sulfobenzylpenicillin disodium salt was administered also by the oral route.

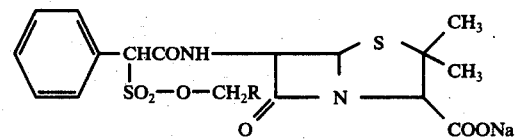

n stands for the number of rats used

| R | Urinary recovery % |
|---|---|
| —CH(CH₃)₂ (—CH with two CH₃) | 6.1 (n=6) |
| —CH₂CH(CH₃)₂ | 7.4 (n=6) |
| —CH₂—C(CH₃)₃ | 4.0 (n=5) |
| —CH(CH₂CH₃)CH₂CH₃ | 6.9 (n=6) |
| —CH(CH₃)CH₂CH₃ | 5.0 (n=5) |
| —C(CH₃)₂CH₂CH(CH₃)₂ | 5.1 (n=5) |
| —CH(CH₃)(CH₂)₇CH₃ | 5.7 (n=5) |
| α-Sulfobenzylpenicillin disodium salt | 0.4 (n=6) |

EXAMPLE 1

In 16 ml. of dry ether is dissolved 2.72 g. of α-2-methylpropylsulfophenylacetic acid, and then 0.94 ml. of thionyl chloride and 0.04 ml. of N,N-dimethylformamide are added. The mixture is refluxed for 5 hours. After the reaction, the mixture is concentrated under reduced pressure to remove the unreacted thionyl chloride to obtain the corresponding acid chloride.

In 6 ml. of dry chloroform is suspended 2.16 g. of 6-aminopenicillanic acid, followed by the addition of 3 ml. of hexamethyldisilazane. The mixture is refluxed under stirring for 1 hour. After the reaction, the mixture is concentrated under reduced pressure at an external temperature of 50° C, whereupon a syrupy residue is obtained.

This syrupy product is dissolved in 120 ml. of dichloromethane and, while the solution is cooled to −40° C, 1.30 ml. of quinoline is added. The acid chloride previously obtained is dissolved in 40 ml. of dichloromethane and added dropwise over a period of 10 minutes. The reaction is further allowed to proceed under cooling with ice for 1 hour. Then, 120 ml. of cold ether, 80 ml. of cold water and 200 ml. of cold ether are added in that order. Then, the mixture is adjusted to pH 2.0 by the addition of 10% hydrochloric acid. The water layer is discarded and the ether layer is obtained. After washing with 80 ml. of cold water, 60 ml. of water is added to the ether layer. To the mixture is gradually added 9.2 ml. of 1N sodium hydroxide aqueous solution. The water layer is harvested and, after the solvent is removed, lyophilized. The procedure yields 4.3 grams of α-2-methylpropylsulfobenzylpenicillin sodium salt, i.e. sodium salt of penicillin (I) wherein R is isopropyl.

IR(KBr, cm$^{-1}$): 3350, 2975, 1770, 1690, 1612, 1520, 1360, 1166, 935, 692

NMR(60MHz, ppm., d$_6$DMSO): 0.80(3H, s.), 0.91(3H, s,), 1.50 (6H, t.), 1.90(1H, mult.), 3.90(1H, s,), 3.95(2H, d.), 5.40(2H, d.), 5.90(1H, s.), 7.42(5H), 9.15(1H, broad).

EXAMPLE 2

A carboxylic acid of general formula II (0.01 mole) is dissolved in 16 ml. of dry ether and 0.94 ml. of thionyl chloride and 0.04 ml. of N,N-dimethylformamide are added.

The mixture is refluxed for 5 hours, at the end of which time it is concentrated under reduced pressure to remove as much unreacted thionyl chloride as possible. Thus the corresponding acid chloride is obtained.

In 6 ml. of dry chloroform is suspended 2.16 g. (0.01 mole) of 6-aminopenicillanic acid, followed by the addition of 3 ml. of hexamethyldisilazane. The mixture is refluxed under stirring for 1 hour. After the reaction, the reaction mixture is concentrated under reduced pressure and at an external temperature of 50° C, whereupon a syrupy residue is obtained. This syrupy product is dissolved in 120 ml. of dichloromethane and the solution is cooled to $-40°$ C. Then, 1.30 ml. of quinoline is added.

The acid chloride obtained above is dissolved in 40 ml. of dichloromethane and the solution is added dropwise over a period of 10 minutes. The mixture is further reacted under cooling with ice for 1 hour. Then, 120 ml. of cold ether, 80 ml. of cold water and 200 ml. of cold ether are added in the order mentioned. Then, the mixture is brought to pH 2.0 with 10% hydrochloric acid. The water layer is discarded and the ether layer is obtained. After washing with 80 ml. of cold water, 60 ml. of water is added to the ether layer. Then, the mixture is adjusted to pH 7.5 by the gradual addition of 1N sodium hydroxide aqueous solution. The water layer is harvested and, after the solvent is removed, lyophilized. The procedure yields the penicillin sodium salt of general formula I' as white to pale yellowish powders.

The infrared absorption and nuclear magnetic resonance spectra of penicillin compounds I' are shown below.

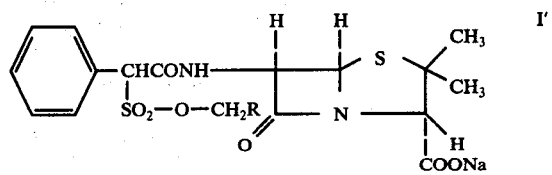

| Compound No. | Branched alkyl R | (Yield) | Infrared absorption spectrum (KBr, cm$^{-1}$) | Nuclear magnetic resonance spectrum (60MHz, ppm., d$_6$DMSO) |
|---|---|---|---|---|
| 1 | —C(CH$_3$)$_3$ | (4.0g) | 3350, 2970, 1770, 1685, 1610, 1520, 1360, 1165, 950, 690 | 0.85(9H,s), 1.30, 1.40, 1.50, 3.80(3H,s), 5.20 (2H,mult), 5.75(1H,s), 7.40(5H), 9.15(1H,broad) |
| 2 | —CH(CH$_3$)CH$_2$CH$_3$ | (3.9g) | 3350, 2970, 1770, 1685, 1610, 1520, 1360, 1168, 945, 735, 692 | 0.83(d), 0.90(t), 1.41, 1.50, 1.59, 3.95(1H,s), 4.09(2H,d), 5.35(2H,mult), 5.90(1H,s), 7.40(5H), 9.10(1H,broad) |
| 3 | —CH$_2$CH(CH$_3$)$_2$ | (4.2g) | 3350, 2960, 1770, 1690, 1610, 1515, 1360, 1166, 930, 730, 690 | 0.82, 0.92, 1.43, 1.50, 1.62, 3.87(1H,s), 4.15 (2H,t), 5.37(2H,mult), 5.90(1H,s), 7.48(5H), 9.15(1H,broad) |
| 4 | —C(CH$_3$)$_2$—CH$_2$—CH$_3$ | (4.0g) | 3350, 2960, 1770, 1690, 1613, 1520, 1360, 1165, 945, 690 | 0.82(s), 1.41, 1.50, 1.60, 3.83(1H,s), 3.80(2H,s), 5.35(2H,mult),5.85(1H,s), 7.33(5H), 9.10(1H,broad) |
| 5 | —CH(CH$_3$)CH$_2$CH$_2$CH$_3$ | (3.8g) | 3350, 2970, 1770, 1690, 1610, 1510, 1360, 1165, 940, 690 | 0.87(t), 0.79, 0.90, 1.40, 1.50, 1.61, 3.96(1H,s), 4.04(2H,d), 5.42(2H,mult), 5.90(1H,s), 7.45(5H), 9.12(1H,broad) |
| 6 | —CHCH(CH$_3$)$_2$ (with additional CH$_3$) — i.e. —CH(CH$_3$)CH(CH$_3$)... [—CHCH< with CH$_3$, CH$_3$ on adjacent carbon and CH$_3$ on the CH] | (4.0g) | 3370, 2970, 1775, 1690, 1610, 1520, 1355, 1165, 935, 690 | 0.81(mult), 1.40, 1.48, 1.59, 3.86(1H,s), 4.03(2H,d), 5.33(2H,mult), 5.86(1H,s), 7.35(5H), 9.10(1H,broad) |
| 7 | —CH(CH$_2$CH$_3$)(CH$_2$—CH$_3$) | (4.1g) | 3350, 2970, 1770, 1690, 1610, 1510, 1355, 1165, 930, 690 | 0.86(t), 1.43, 1.51, 1.62, 3.91(1H,s), 4.09(2H,d), 5.37 (2H,mult), 5.85(1H,s), 7.35 (5H), 9.05(1H,mult) |
| 8 | —CH$_2$C(CH$_3$)$_3$ | (4.0g) | 3350, 2960, 1770, 1690, 1612, 1515, 1360, 1163, 937, 730, 690 | 0.89(9H,s), 1.45, 1.58, 1.67, 3.92(1H,s), 4.12(2H,t), 5.37 (2H,mult), 5.88(1H,d), 7.40 (5H), 9.10(1H,broad) |

-continued

| Compound No. | Branched alkyl R | (Yield) | Infrared absorption spectrum (KBr, cm⁻¹) | Nuclear magnetic resonance spectrum (60MHz, ppm., d₆DMSO) |
|---|---|---|---|---|
| 9 | —CH₂CH(CH₃)CH₂CH₃ | (4.0g) | 3350, 2960, 1770, 1690, 1610, 1515, 1360, 1165, 930, 690 | 0.87(t), 0.81, 0.90, 1.42, 1.50, 1.61, 3.87(1H,s), 4.13(2H,t), 5.40(2H,mult), 5.91(1H,s), 7.46(5H), 9.13 (1H) |
| 10 | —CH₂CH₂CH(CH₃)₂ | (3.9g) | 3350, 2960, 1770, 1685, 1610, 1520, 1355, 1165, 935, 690 | 0.80, 0.85, 1.41, 1.50, 1.62, 3.86(1H,s), 4.12(2H,t), 5.36 (2H,mult), 5.85(1H,s), 7.37 (5H), 9.10(1H,broad) |
| 11 | —C(CH₃)₂CH₂CH₂CH₃ | (3.6g) | 3350, 2960, 1770, 1690, 1610, 1520, 1355, 1165, 954, 690 | 0.80(s), 1.08, 1.36, 1.46, 1.59, 3.85(3H,s), 5.30(2H, mult), 5.87(1H,s), 7.38(5H), 9.10(1H,broad) |
| 12 | —CH(CH₃)CH₂CH₂CH₂CH₃ | (4.1g) | 3360, 2970, 1775, 1695, 1615, 1520, 1360, 1170, 940, 692 | 0.88(t), 0.80, 0.91, 1.41, 1.52, 1.63, 3.95(1H,s), 4.05(2H,d), 5.45(2H,mult), 5.95(1H,s), 7.45(5H), 9.20 (1H,broad) |
| 13 | —CH(CH₃)CH₂CH(CH₃)₂ | (4.3g) | 3350, 2970, 1770, 1690, 1610, 1515, 1360, 1165, 935, 690 | 0.82(mult), 1.42, 1.51, 1.61, 3.84(1H,s), 4.00 (2H,d), 5.40(2H,mult), 5.88 (1H,s), 7.35(5H), 9.15(1H, broad) |
| 14 | —C(CH₃)₂CH(CH₃)₂ | (3.0g) | 3400, 2970, 1770, 1685, 1610, 1520, 1355, 1165, 940, 690 | 0.79(s), 0.73, 0.82, 1.40, 1.50, 1.61, 3.93(3H,s), 5.40(2H,mult), 5.98(1H,s), 7.43(5H), 9.15(1H,broad) |
| 15 | —CH(CH₂CH₃)CH(CH₃)₂ | (4.2g) | 3400, 2980, 1770, 1690, 1610, 1520, 1360, 1170, 930, 690 | 0.79(s), 0.89, 1.42, 1.51, 1.62, 3.95(1H,s), 4.15(2H, d), 5.40(2H,mult), 5.92 (1H,s), 7.45(5H), 9.15(1H, broad) |
| 16 | —CH(CH₂CH₃)CH₂CH₂CH₃ | (4.3g) | 3350, 2960, 1770, 1690, 1610, 1520, 1355, 1165, 935, 690 | 0.91(mult), 1.10, 1.40, 1.50, 1.60, 3.92(1H,s), 4.03(2H,d), 5.35(2H,mult), 5.88(1H,s), 7.45(5H), 9.15(1H,broad) |
| 17 | —CH₂(CH₂)₂CH(CH₃)₂ | (4.0g) | 3350, 2960, 1770, 1690, 1615, 1520, 1360, 1165, 930, 690 | 0.77, 0.89, 1.25(s), 1.39, 1.50, 1.60, 3.85(1H,s), 4.00 (2H,t), 5.35(2H,mult), 5.91 (1H,s), 7.45(5H), 9.05(1H, broad) |
| 18 | —C(CH₃)(CH₂CH₃)CH₂CH₃ | (3.9g) | 3350, 2970, 1770, 1690, 1610, 1515, 1360, 1165, 930, 690 | 0.84(t), 1.41, 1.50, 1.60, 3.82(3H,s), 5.25(2H,mult), 5.80(1H,s), 7.40(5H), 9.20 (1H,broad) |
| 19 | —C(CH₃)₂CH₂CH(CH₃)₂ | (4.4g) | 3350, 2970, 1770, 1690, 1610, 1520, 1360, 1165, 940, 840, 690 | 0.78, 0.88, 0.84(s), 1.05(d), 1.37, 1.45, 1.56, 3.76(2H,s), 3.85(1H,s), 5.35(2H,mult), 5.83(1H,s), 7.35(5H), 9.05 (1H,mult) |
| 20 | —CH(CH₂CH₃)CH₂CH(CH₃)₂ | (4.2g) | 3370, 2970, 1770, 1690, 1615, 1518, 1355, 1165, 925, 685 | 0.78, 0.85, 1.10(t), 1.40, 1.50, 1.62, 3.89(1H,s), 4.00 (2H,d), 5.30(2H,mult), 5.85 (1H,s), 7.40(5H), 9.20(1H, broad) |
| 21 | —CH(CH₂CH₃)CH₂CH₂CH₂CH₃ | (4.2g) | 3350, 2960, 1770, 1690, 1610, 1520, 1360, 1168, 933, 690 | 0.90(mult), 1.23(s), 1.43, 1.52, 1.63, 3.95(1H,s), 4.11 (2H,d), 5.40(2H,mult), 5.90 (1H,s), 7.45(5H), 9.15(1H, broad) |
| 22 | —CH₂(CH₂)₃CH(CH₃)₂ | (4.0g) | 3350, 2960, 1770, 1690, 1610, 1520, 1360, 1165, 930, 690 | 0.78, 0.89, 1.18(s), 1.40, 1.49, 1.59, 3.91(1H,s), 4.12 (2H,t), 5.40(2H,mult), 5.91 (1H,s), 7.42(5H), 9.05(1H, broad) |
| 23 | —C(CH₃)₂CH₂(CH₂)₂CH₃ | (4.5g) | 3370, 2970, 1770, 1690, 1610, 1520, 1357, 1167, 945, 690 | 0.85(s), 1.14, 1.40, 1.49, 1.60, 3.84(3H,s), 5.37(2H, mult), 5.86(1H,s), 7.40(5H), 9.15(1H,broad) |

-continued

| Compound No. | Branched alkyl R | (Yield) | Infrared absorption spectrum (KBr, cm$^{-1}$) | Nuclear magnetic resonance spectrum (60MHz, ppm., d$_6$DMSO) |
|---|---|---|---|---|
| 24 | —CH(CH$_3$)CH$_2$CH$_2$CH$_3$ with CH(CH$_3$)$_2$ branch | (4.2g) | 3350, 2970, 1770, 1690, 1615, 1525, 1360, 1170, 935, 690 | 0.78, 0.88, 0.91, 1.39, 1.49, 1.60, 3.98(1H,s), 4.07(2H,d), 5.42(2H,mult), 5.82(1H,s), 7.40(5H), 9.15(1H,broad) |
| 25 | —CH(CH$_3$)CH$_2$CH$_2$CH(CH$_3$)$_2$ | (4.3g) | 3350, 2960, 1770, 1690, 1610, 1525, 1355, 1165, 935, 690 | 0.77, 0.88, 1.20(s), 1.44, 1.51, 1.63, 3.90(1H,s), 3.98(2H,d), 5.42(2H,mult), 5.90(1H,s), 7.35(5H), 9.10(1H, broad) |
| 26 | —C(CH$_2$CH$_3$)$_3$ | (4.0g) | 3350, 2960, 1770, 1690, 1610, 1510, 1360, 1160, 930, 690 | 0.84(t), 1.40, 1.49, 1.60, 3.83(3H,s), 5.40(2H,mult), 5.82(1H,s), 7.40(5H), 9.05(1H,broad) |
| 27 | —CH$_2$CH(CH$_3$)CH$_2$C(CH$_3$)$_3$ | (4.4g) | 3350, 2960, 1770, 1690, 1612, 1360, 1165, 930, 730, 690 | 0.87(s), 1.30–1.70, 1.43, 1.50, 1.62, 3.92(1H,s), 4.20(2H,t), 5.40(2H,mult), 5.90(1H,s), 7.45(5H), 9.10(1H, broad) |
| 28 | —C(CH$_3$)$_2$CH$_2$CH$_2$CH(CH$_3$)$_2$ | (4.3g) | 3350, 2960, 1770, 1690, 1615, 1520, 1360, 1160, 930, 690 | 0.80, 0.85(s), 0.91, 1.20(s), 1.35, 1.45, 1.55, 3.82(3H,s), 5.35(2H,mult), 5.86(1H,s), 7.37(5H), 9.10(1H,broad) |
| 29 | —CH(CH$_3$)CH$_2$CH(CH$_3$)CH(CH$_3$)$_2$ | (4.1g) | 3350, 2960, 1770, 1690, 1610, 1520, 1360, 1160, 930, 690 | 0.79, 0.89, 1.39, 1.50, 1.60, 3.98(1H,s), 4.05(2H,d), 5.43(2H,mult), 5.90(1H,s), 7.45(5H), 9.10(1H,broad) |
| 30 | —C(CH$_3$)$_2$(CH$_2$)$_4$CH$_3$ | (4.5g) | 3350, 2960, 1770, 1690, 1610, 1520, 1355, 1165, 935, 690 | 0.82(s), 0.89, 1.18(s), 1.33, 1.42, 1.51, 3.85(3H,s), 5.34(2H,mult), 5.82(1H,s), 7.34(5H), 9.05(1H,broad) |
| 31 | —CH[(CH$_2$)$_3$CH$_3$][CH$_2$(CH$_2$)$_2$CH$_3$] | (4.3g) | 3400, 2950, 1770, 1685, 1613, 1358, 1168, 935, 690 | 0.88(t), 1.22(s), 1.43, 1.52, 1.62, 3.93(1H,s), 4.10(2H,d), 5.40(2H,mult), 5.93(1H,s), 7.45(5H), 9.13(1H,broad) |
| 32 | —C(CH$_3$)$_2$CH$_2$(CH$_2$)$_2$CH(CH$_3$)$_2$ | (5.0g) | 3350, 1770, 1690, 1610, 1365, 1168, 950, 692, 2960 | 0.85(s), 0.82, 0.91, 1.16(s), 1.43, 1.50, 1.60, 3.85(3H,s), 5.40(2H,mult), 5.90(1H,s), 7.40(5H), 9.10(1H,broad) |
| 33 | —CH$_2$(CH$_2$)$_5$CH(CH$_3$)$_2$ | (4.6g) | 3350, 2970, 1770, 1690, 1615, 1520, 1360, 1160, 930, 690 | 0.80, 0.90, 1.15(s), 1.41, 1.50, 1.61, 3.86(1H,s), 4.02(2H,t), 5.38(2H,mult), 5.90(1H,s), 7.40(5H), 9.06(1H,broad) |
| 34 | —CH(CH$_2$CH$_3$)(CH$_2$)$_3$CH(CH$_3$)$_2$ | (4.7g) | 3350, 2960, 1770, 1690, 1620, 1520, 1360, 1165, 930, 690 | 0.78, 0.91, 1.20(s), 1.43, 1.53, 1.63, 3.92(1H,s), 4.05(2H,d), 5.41(2H,mult), 5.85(1H,s), 7.42(5H), 9.07(1H, broad) |
| 35 | —C(CH$_2$CH$_3$)$_2$CH$_2$CH(CH$_3$)$_2$ | (4.9g) | 3350, 2950, 1770, 1690, 1615, 1520, 1360, 1165, 930, 690 | 0.80, 0.89, 1.38, 1.48, 1.59, 3.83(3H,s), 5.40(2H,mult), 5.83(1H,s), 7.38(5H), 9.08(1H,broad) |
| 36 | —CH(CH$_3$)(CH$_2$)$_7$CH$_3$ | (5.3g) | 3350, 2950, 1770, 1690, 1615, 1520, 1360, 1167, 940, 730, 689 | 0.82(d), 0.85, 1.21(s), 1.38, 1.48, 1.60, 3.88(1H,s), 3.95(d), 5.30(2H,mult), 5.82(1H,s), 7.35(5H), 9.10(1H,broad) |

-continued

| Compound No. | Branched alkyl R | (Yield) | Infrared absorption spectrum (KBr, cm$^{-1}$) | Nuclear magnetic resonance spectrum (60MHz, ppm., d$_6$DMSO) |
|---|---|---|---|---|
| 37 | −CH$_2$(CH$_2$)$_6$CH(CH$_3$)$_2$ | (5.2g) | 3350, 2950, 1770, 1690, 1615, 1520, 1365, 1165, 930, 690 | 0.77, 0.89, 1.25(s), 1.45, 1.53, 1.62, 3.96(1H,s), 4.10 (2H,t), 5.48(2H,mult), 5.92 (1H,s), 7.48(5H), 9.20(1H, broad) |
| 38 | −C(CH$_2$CH$_3$)$_2$−CH$_2$CH$_2$CH(CH$_3$)$_2$ | (5.3g) | 3360, 2950, 1770, 1690, 1620, 1520, 1365, 1165, 930, 690 | 0.79, 0.92, 1.37, 1.46, 1.58, 3.86(3H,s), 5.38(2H,mult), 5.82(1H,s), 7.36(5H), 9.20( 1H,broad) |
| 39 | −CH(CH$_2$CH$_3$)−(CH$_2$)$_3$−CH(CH$_3$)$_2$ | (5.4g) | 3350, 2950, 1770, 1690, 1615, 1530, 1360, 1165, 930, 690 | 0.79, 0.89, 1.21(s), 1.41, 1.50, 1.60, 3.89(1H,s), 4.01 (2H,d), 5.39(2H,mult), 5.83 (1H,s), 7.39(5H), 9.12(1H, broad) |
| 40 | −CH(CH$_3$)(CH$_2$)$_9$CH$_3$ | (5.0g) | 3400, 2950, 1780, 1690, 1620, 1530, 1365, 1170, 950, 692 | 0.85, 0.92, 1.30(s), 1.48, 1.56, 1.67, 3.94(1H,s), 4.05(2H,d), 5.40(2H,mult), 5.90(1H,s), 7.45(5H), 9.10 (1H,broad) |
| 41 | −CH(CH$_2$CH$_3$)(CH$_2$)$_7$CH(CH$_3$)$_2$ | (5.3g) | 3350, 2960, 1770, 1690, 1610, 1530, 1365, 1170, 935, 690 | 0.77, 0.90, 1.25(s), 1.39, 1.49, 1.60, 3.92(1H,s), 4.10(2H,d), 5.40(2H,mult), 5.85(1H,s), 7.45(5H), 9.10 (1H,broad) |
| 42 | −CH(CH$_2$CH$_3$)(CH$_2$)$_9$CH$_3$ | (5.0g) | 3450, 2940, 1770, 1685, 1615, 1530, 1360, 1168, 932, 690 | 0.83, 1.20(s), 1.37, 1.48, 1.60, 3.85(1H,s), 4.00(2H, d), 5.35(2H,mult), 5.80(1H, s), 7.30(5H), 9.00(1H,broad) |
| 43 | −CHCH$_2$(CH$_2$)$_5$CH(CH$_3$)−CH$_3$ with CH(CH$_3$)$_2$ branch | (4.9g) | 3350, 2950, 1770, 1690, 1610, 1530, 1365, 1165, 930, 690 | 0.80, 0.91, 1.23(s), 1.39, 1.50, 1.60, 3.89(1H,s), 4.00 (2H,d), 5.38(2H,mult), 5.82 (1H,s), 7.36(5H), 9.12(1H, broad) |
| 44 | −CHCH$_2$(CH$_2$)$_8$CH$_3$ with CH(CH$_3$)$_2$ branch | (4.9g) | 3370, 2950, 1780, 1690, 1615, 1530, 1367, 1170, 940, 692 | 0.78, 0.87, 0.90, 1.25(s), 1.40, 1.50, 1.62, 4.02(1H, s), 4.10(2H,d), 5.45(2H, mult), 5.90(1H,s), 7.42(5H), 9.20(1H,broad) |

EXAMPLE 3

A carboxylic acid of general formula II (0.01 mole) is dissolved in 16 ml. of dry ether and 0.94 ml. of thionyl chloride and 0.04 ml. of N,N-dimethylformamide are added.

The mixture is refluxed for 5 hours. After the reaction has been completed, the reaction mixture is concentrated under reduced pressure to remove as much unreacted thionyl chloride as possible to obtain the corresponding acid chloride as the residue. The acid chloride is dissolved in 10 ml. of anhydrous ether.

2.16 g. (0.01 mol) of 6-aminopenicillanic acid is dissolved into a mixture of 30 ml. water and 10 ml. 1N sodium hydroxide aqueous solution under cooling with ice, followed by the addition of 2.52 g. sodium bicarbonate as well as 36 ml. of ether and vigorous stirring. Then the above ethereal solution of acid chloride is dropwise added to the mixture, the addition taking 10 minutes. The mixture is stirred further for 10 minutes. After the reaction, the aqueous phase is separated and washed with 20 ml. of ether. To the aqueous layer is added 30 ml. of ether, and the resulting mixture is adjusted to pH 2.0 by the addition of 10% hydrochloric acid. The aqueous layer is discarded and the organic layer is washed with 80 ml. of cold water. The organic layer is incorporated with 60 ml. of water, and the resulting mixture is adjusted to pH 7.5 by the addition of 1N sodium hydroxide aqueous solution. The aqueous layer is separated, concentrated under reduced pressure and lyophilized to obtain the following penicillin sodium salts I':

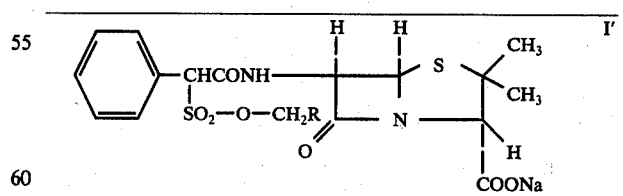

| Compound No. | Branched alkyl R | Yield (g) |
|---|---|---|
| 3 | −CH$_2$CH(CH$_3$)$_2$ | 3.4 |
| 7 | −CH(CH$_2$−CH$_3$)−CH$_2$CH$_3$ | 3.2 |

-continued

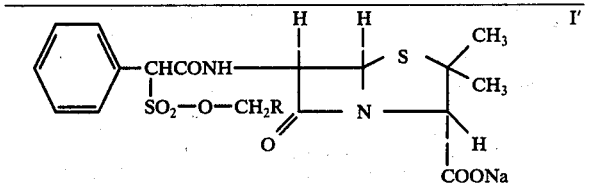

| Compound No. | Branched alkyl R | Yield (g) |
|---|---|---|
| 8 | —CH$_2$—CH(CH$_3$)—CH$_3$ with CH$_3$ | 3.2 |
| 19 | —C(CH$_3$)(CH$_3$)—CH$_2$—CH(CH$_3$)(CH$_3$) | 3.3 |

EXAMPLE 4

By the same procedures as those of Example 3, the penicillin sodium salt I' wherein R is isopropyl is obtained. Yield is 3.0 g.

EXAMPLE 5

The method of Example 2 is repeated, except for slightly modifying the recovery means, as follows.

After adjusting the reaction mixture to pH 2.0 by the addition of 10% hydrochloric acid, the water layer is discarded. The ether layer is washed with 80 ml. cold water, dehydrated over anhydrous sodium sulphate and concentrated under reduced pressure to obtain the penicillin compound I as a yellow solid in free acid form.

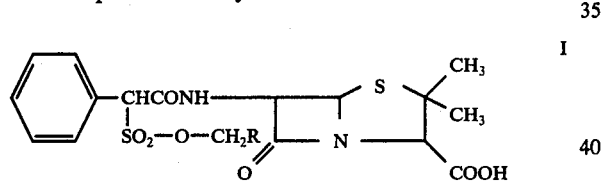

After adjusting the reaction mixture to pH 2.0 by the addition of 10% hydrochloric acid, the water layer is discarded. The ether layer is washed with 80 ml. cold water, dehydrated over anhydrous sodium sulphate and concentrated under reduced pressure to obtain the penicillin compound I wherein R is isopropyl in free acid form. The yield is 5.01 g.

| Infrared absorption spectrum (KBr,cm$^{-1}$) | Nuclear magnetic resonance spectrum (60MHz,ppm, d$_6$DMSO) |
|---|---|
| 3350, 2980, 1790, 1760, 1690, 1530, 1460, 1360, 1205, 1170, 1060, 938, 842, 693 | 0.72, 0.82, 1.30, 1.40, 1.52, 1.80 (mult.,1H), 3.82(d., 2H), 4.10(s,1H), 5.35(mult.,2H), 5.65(d, 1H), 7.30(5H), 9.00 (d,1H). |

What is claimed is:

1. A penicillin compound selected from the group consisting of a compound of the formula

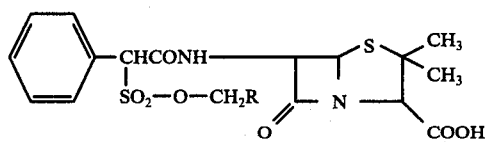

wherein R is isopropyl,

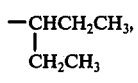

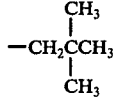

or

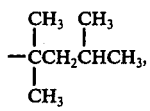

| Compound No. | Branched alkyl R | (Yield) | Infrared absorption spectrum (KBr, cm$^{-1}$) | Nuclear magnetic resonance spectrum (60MHz, ppm., d$_6$DMSO) |
|---|---|---|---|---|
| 3 | —CH$_2$CH(CH$_3$)(CH$_3$) | (4.90g) | 3350, 2960, 1790, 1760, 1690, 1530, 1370, 1170, 935, 732, 692 | 0.77, 0.86, 1.50(mult), 1.36, 1.45, 1.56, 4.17(s,1H), 4.17(t,2H), 5.40(mult), 5.70(d,1H), 7.45(5H), 9.10 (d,1H) |
| 7 | —CH(CH$_2$CH$_3$)CH$_2$CH$_3$ | (5.45g) | 3330, 2970, 1785, 1760, 1690, 1530, 1360, 1170, 930, 692 | 0.83, 1.38, 1.48, 1.60, 4.07 (d,2H), 4.20(s,1H), 5.45(mult, 2H), 5.73(d,1H), 7.37(5H), 9.09(mult) |
| 8 | —CH$_2$C(CH$_3$)(CH$_3$)—CH$_3$ | (5.30g) | 3350, 2960, 1788, 1760, 1695, 1530, 1365, 1167, 940, 730, 692 | 0.83(s,9H), 1.37, 1.49, 1.60, 4.17(t,2H), 4.18(s,1H), 5.47 (mult,2H), 5.70(d,1H), 7.39 (5H), 9.15(d,1H) |
| 19 | —C(CH$_3$)(CH$_3$)—CH$_2$CH(CH$_3$)(CH$_3$) | (5.80g) | 3350, 2970, 1790, 1760, 1690, 1530, 1360, 1170, 945, 840, 692 | 0.75, 0.78, 0.82, 1.00(d), 1.32, 1.42, 1.56, 3.76(s, 2H), 3.85(s,1H), 5.38(mult, 2H), 5.72(s,1H), 7.30(5H), 9.05(d,1H) |

EXAMPLE 6

The method of Example 1 is repeated, except for slightly modifying the recovery means as follows.

and a pharmaceutically acceptable salt thereof.

2. A penicillin compound as claimed in claim 1, wherein R is isopropyl.

3. A penicillin compound as claimed in claim 1, wherein R is

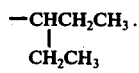

4. A penicillin compound as claimed in claim 1, wherein R is

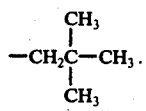

5. A penicillin compound as claimed in claim 1, wherein R is

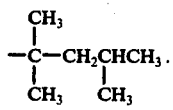

6. A penicillin compound selected from the group consisting of a compound of the formula

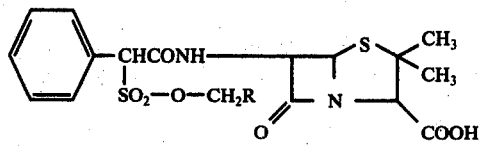

wherein R is

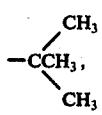

and a pharmaceutically acceptable salt thereof.

7. A compound of the formula

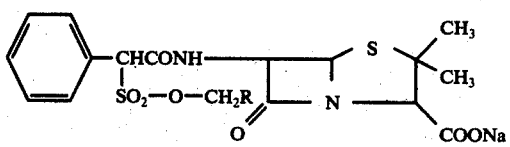

wherein R is isopropyl.

* * * * *